United States Patent [19]

Sato

[11] 4,097,478
[45] Jun. 27, 1978

[54] PROCESS FOR PREPARING PYRAZINES
[75] Inventor: Kanji Sato, Fuji, Japan
[73] Assignee: Tokai Denka Kogyo Kabushiki Kaisha, Ohte, Japan
[21] Appl. No.: 783,172
[22] Filed: Mar. 31, 1977
[30] Foreign Application Priority Data Sep. 20, 1976 Japan .................. 51-111717

[51] Int. Cl.² .................. C07D 241/04; C07D 241/06
[52] U.S. Cl. .................. 544/353; 544/410
[58] Field of Search .......... 260/250 B, 250 BC, 250 Q

[56] References Cited

U.S. PATENT DOCUMENTS

B 280,015 1/1975 Heinz-Werner et al. ........ 260/250 B
3,219,707 11/1965 Patton, Jr. et al. ............. 260/250 B Primary Examiner—Jose Tovar

[57] ABSTRACT

According to the present invention, there is provided a process for preparing pyrazines characterized in that a diol represented by the formula

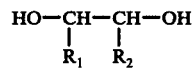

wherein $R_1$ and $R_2$ are each a hydrogen atom or a hydrocarbon radical, and a diamine represented by the formula

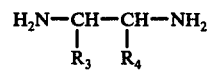

wherein $R_3$ and $R_4$ are each a hydrogen atom or a hydrocarbon radical, are subjected to a gas phase contact reaction in the presence of a zinc-containing catalyst.

7 Claims, No Drawings

PROCESS FOR PREPARING PYRAZINES

BACKGROUND OF THE INVENTION

1. Field of the Invention

The present invention relates to a process for preparing pyrazines by a gas phase contact reaction in the presence of a catalyst using diol and diamine as the starting material.

2. Description of the Prior Art

Pyrazines are used mainly as perfumes and are also useful as the starting material of medicines and agricultural chemicals.

Pyrazines have heretofore been prepared mainly by a gas phase dehydrogenation reaction of piperazines. However, this method is not practical because the starting piperazines are expensive and besides many of them are difficult to obtain. There has also been reported a method of preparing pyrazines by a gas phase contact reaction in the presence of an alumina catalyst or a copper- and chromium-containing catalyst. In both methods, however, the yield is low and there is a considerable by-production of pyrazines and piperazines other than the object substance. Separation sometimes becomes difficult according to the kind of pyrazines by-produced, and in many cases it is impossible to obtain a pure product. Furthermore, the duration of catalyst activity is short. Thus, the conventional methods mentioned above have such drawbacks and are not practical.

SUMMARY OF THE INVENTION

The present invention is based on the finding that if a diol and a diamine are subjected to a gas phase contact reaction in the presence of a zinc-containing catalyst, the yield of the resulting pyrazines is remarkably improved as compared wth conventional methods. Furthermore, the present invention easily affords a high purity product with scarcely any by-production of pyrazines, and has features not recognized in conventional catalysts such as a long duration of the catalyst activity.

DESCRIPTION OF THE INVENTION

The present invention resides in a process for preparing pyrazines characterized in that a diol represented by the formula

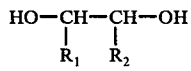

wherein $R_1$ and $R_2$ are each a hydrogen atom or a hydrocarbon radical, and a diamine represented by the formula

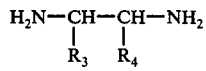

wherein $R_3$ and $R_4$ are each a hydrogen atom or a hydrocarbon radical, are subjected to a gas phase contact reaction in the presence of a zinc-containing catalyst. The process of the present invention is practised in a known manner except the use of a catalyst of the aforementioned composition. That is, the starting diol and diamine, separately or as a mixture of both, as they are or after dissolved in a suitable solvent, are gasified and, as they are or after dilution with for example an inert gas, are fed to a reactor which is heated at a high temperature and which contains the catalyst of the present invention.

In the starting diol and diamine of the present invention, the hydrocarbon radical represented by the symbols $R_1 - R_4$ indicates aliphatic, aromatic and alicyclic hydrocarbon radicals.

Examples of diols are ethylene glycol, 1,2-propylene glycol, 1,2-butanediol, 2,3-butanediol, 1,2-cycohexanediol, 1,2-cyclopentanediol, 1,2-pentanediol, 2,3-pentanediol, 3-methyl-1,2-butanediol, styrene glycol, and 3,4-hexanediol.

Examples of diamines are ethylenediamine, 1,2-diaminopropane, 1,2-diaminobutane, 2,3-diaminobutane, 1,2-diaminocyclohexane, O-phenylenediamine, and 2,3-diaminotoluene.

The pyrazines prepared by the present invention differ according to the kind of the starting diol and diamine used. For example, in case ethylene glycol and ethylenediamine are used, pyrazine is obtained; in case 1,2-propylene glycol and ethylenediamine as used, 2-methylpyrazine is obtained; and the use of 2,3-butanediol and 1,2-diaminopropane affords 2,3,5-trimethylpyrazine.

As to the mixing ratio of the starting diol and diamine, the two may be used even in such a mixing ratio as either diol or diamine is larger in ratio. Even if diol is used in an amount larger than the reaction equimolar amount, there is little by-production of pyrazines, but in case the amount of diamine used is larger, pyrazines other than the object substance are liable to be by-produced. Preferably, diol and diamine are mixed together in a reaction equimolar amount.

The catalyst used in the present invention contains zinc as a component and usually is used as a zinc oxide. As the carrier of this catalyst may be used silica, alumina, silica-alumina, and a diatomaceous earth. Furtermore, in combination therewith, other metals, for example, cobalt, nickel, iron, aluminum, and chromium, are also employable. In these cases, the content of zinc is not specially restricted, but preferably it is above 10%.

The regeneration of catalyst is carried out by conventional methods. For example, a catalyst whose activity has lowered is first subjected to steaming and then to air oxidation at 400–500° C., whereby it can be regenerated.

The reaction temperature of the starting diol and diamine using the catalyst of the present invention is suitably in the range of from 300° to 600° C. and preferably from 400° to 500° C. If the reaction temperature is below the optimum temperature, both the conversion of the starting materials and the yield of pyrazines will be low, and if it is thereabove, the conversion will be high, but the yield will be low.

The space velocity in introducing a mixed gas containing the starting diol and diamine into a reactor can be varied in wide range though it differs according to the particle size of the catalyst used. For example, in case particles with a diameter about 5 mm × 10 mm are used, the space velocity is usually in the range of from 10 to 10,000 1/1 (catalyst)·hr. and preferably from 100 to 1,000 1/1 (catalyst)·hr. For about 15-mesh particles, the space velocity ranges from 100 to 50,000 1/1 (catalyst)·hr. and preferably from 500 to 5,000 1/1 (catalyst)·hr.

The solvent and inert gas for dilution which may be employed in the present invention are not specially restricted, provided that they should be stable under the reaction condition. As a solvent, for example, water, benzene, toluene, xylene, and cyclohexane may be used. As an inert gas for dilution, for example, argon, helium, hydrogen, nitrogen and a lower hydrocarbon are employable.

The product after the completion of reaction is separated from the reaction mixture and purified according to conventional methods, for example, by means of rectification. In case water is used as solvent, almost all pyrazines are distilled out as an azeotropic mixture by rectification. To the azeotropic mixture is then added an anhydrous caustic soda in a molar ratio of water contained in the azeotropic mixture to caustic soda in the range of from 1:1 to 10:1, which are then mixed together at a temperature above the melting point of each pyrazines and dehydrated. The layer of each pyrazines is then separated and rectified, whereby the separation and purification of each pyrazines can be made in high purity.

DESCRIPTION OF PREFERRED EMBODIMENTS

The following examples are given to further illustrate the present invention, but the present invention is not limited thereto.

The conversion and the yield in the following examples both have been calculated on the basis of the amount of the starting diamine used, the conversion indicating the ratio of the reacted diamine to the diamine introduced, and the yield being a value for the converted diamine.

EXAMPLES 1 – 10

A zinc oxide catalyst in the form of 10 to 15-mesh particles was prepared by the conventional method. 40 ml of the catalyst was charged into a stainless steel reaction tube having an inside diameter of 10 mm. While the reacting part of the reaction tube was held at 460°–470° C., an equimolar mixture of diol and diamine was diluted with water to give a 50% (v/v) aqueous solution, which was gasified at a rate of 2 ml/min. and then passed through the catalyst. After the reaction had been continued for 1 hour, the reaction product was cooled and recovered and then subjected to an analysis by means of gas chromatography. The results are shown in table below.

In the preparation of pyrazine, there was no by-production of other pyrazines. In the preparation of other pyrazines, an extremely small amount of pyrazine was recognized in the by-product in all the cases, but no other pyrazines were recognized therein.

| Example No. | Starting Material | Object Substance | Conversion | Yield |
|---|---|---|---|---|
| 1 | ethylene glycol, ethylenediamine | pyrazine | 100% | 55% |
| 2 | 1,2-propylene glycol, ethylenediamine | 2-methylpyrazine | " | 70 |
| 3 | 1,2-butanediol, ethylenediamine | 2-ethylpyrazine | " | 70 |
| 4 | 2,3-butanediol, ethylenediamine | 2,3-dimethylpyrazine | " | 73 |
| 5 | 1,2-propylene glycol, 1,2-diaminopropane | a mixture of 2,5-dimethylpyrazine and 2,6-dimethylpyrazine | " | 70 |
| 6 | 1,2-butanediol, 1,2-diaminobutane | a mixture of 2,5-diethylpyrazine and 2,6-diethylpyrazine | " | 73 |
| 7 | 2,3-butanediol, 1,2-diaminopropane | 2,3,5-trimethylpyrazine | " | 75 |
| 8 | 1,2-butanediol, 2,3-diaminobutane | 2,3-dimethyl 5-ethylpyrazine | " | 73 |
| 9 | 2,3-butanediol, 2,3-diaminobutane | 2,3,5,6-tetramethylpyrazine | " | 78 |
| 10 | ethylene glycol, 1,2-diaminocyclohexane | 5,6,7,8-tetrahydroquinoxaline | " | 66 |

EXAMPLE 11

A 10 to 15-mesh catalyst composed of 50% zinc oxide and 50% aluminum oxide was prepared by the conventional method. As the starting material, an equimolar mixture of 1,2-butanediol and ethylenediamine was diluted with water to give a 50% (v/v) aqueous solution. And a reaction was made under the same reaction conditions as in Examples 1 – 10. As a result, the conversion and the yield of 2-ethylpyrazine were 100% and 72%, respectively. An extremely small amount of pyrazine was recognized as a by-product, but any other pyrazines except the object substance were recognized.

EXAMPLE 12

200 ml. of a commercially available zinc oxide catalyst (G-72-D), a product of NISSAN-Girdler, shape: extrusion type 3/16 inch) was charged into a stainless steel reaction tube having an inside diameter of 23 mm. While the reacting part of the reaction tube was held at 460–490° C., an equimolar mixture of 1,2-propylene glycol and ethylenediamine was diluted with water to give a 50% (v/v) aqueous solution, which was gasified at a rate of 3 ml/min. and then passed through the catalyst, and thus a reaction was made.

The reaction product was recovered and subjected to an analysis by means of gas chromatography. As a result, the initial conversion and yield of 2-methylpyrazine were 100% and 70%, respectively.

After reaction for 20 consecutive hours, the conversion and the yield of 2-methylpyrazine were 95% and 65%, respectively. Thus, the catalyst activity lasted for a long time. In both cases, an extremely small amount of pyrazine was recognized in the by-product, but other pyrazines were not recognized therein.

I claim:

1. A process for preparing pyrazines characterized in that a diol represented by the formula

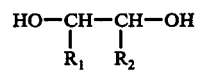

wherein $R_1$ and $R_2$ are each a hydrogen atom or a hydrocarbon radical selected from the group consisting of aliphatic, aromatic and alicylic hydrocarbon radicals, and a diamine represented by the formula

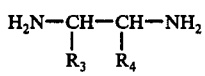

wherein $R_3$ and $R_4$ are each a hydrogen atom or a hydrocarbon radical selected from the group consisting of aliphatic, aromatic and alicyclic hydrocarbon radicals, are subjected to a gas phase contact reaction in the presence of a catalyst containing zinc or zinc in combination with at least one other metal selected from the group consisting of cobalt, nickel, iron, aluminum and chromium.

2. A process according to claim 1 wherein the catalyst is zinc oxide.

3. A process according to claim 1 wherein one member selected from the group consisting of silica, alumina, silica-alumina, and a diatomaceous earth, is used as a carrier for said catalyst.

4. A process according to claim 1 wherein the catalyst contains above 10% of zinc and at least one metal component selected from the group consisting of cobalt, nickel, iron, aluminum, and chromium.

5. A process according to claim 1 wherein the reaction of said diol and said diamine is carried out at a temperature in the range of from 300° to 600° C.

6. A process according to claim 1 wherein water, benzene, toluene, xylene, or cyclohexane, is used as solvent.

7. A process according to claim 1 wherein argon, helium, hydrogen, nitrogen or a lower hydrocarbon, is used as an inert gas for dilution.

* * * * *